US006079634A

United States Patent [19]

Noakes et al.

[11] Patent Number: 6,079,634

[45] Date of Patent: Jun. 27, 2000

[54] ELECTROSTATIC SPRAYING

[75] Inventors: Timothy James Noakes, Clwyd; Maurice Joseph Prendergast, Bracknell; Michael Leslie Green, Nannereh, all of United Kingdom

[73] Assignee: The Procter & Gamble Company, Cincinnati, Ohio

[21] Appl. No.: 08/985,993

[22] Filed: Dec. 5, 1997

Related U.S. Application Data

[63] Continuation of application No. PCT/GB96/01286, May 30, 1996.

[51] Int. Cl.[7] .................................................... A01G 23/10

[52] U.S. Cl. .............................. 239/3; 239/690; 239/692; 239/704; 239/706; 128/200.14; 128/204.13

[58] Field of Search ................................ 239/3, 690, 692, 239/704, 706, 337, 338; 128/200.14, 204.13

[56] References Cited

U.S. PATENT DOCUMENTS

| | | | |
|---|---|---|---|
| 4,829,996 | 5/1989 | Noakes et al. | 128/200.14 |

FOREIGN PATENT DOCUMENTS

| | | |
|---|---|---|
| 0 224 352 | 6/1987 | European Pat. Off. . |
| 0 234 842 | 9/1987 | European Pat. Off. . |
| 0 501 725 | 9/1992 | European Pat. Off. . |
| 94/14543 | 9/1994 | WIPO . |
| 94/19042 | 9/1994 | WIPO . |

*Primary Examiner*—Joseph A. Kaufman
*Assistant Examiner*—David Deal
*Attorney, Agent, or Firm*—William Scott Andes

[57] ABSTRACT

An electrostatic spraying device is disclosed which is suitable for, but not limited to, dispensing an electrostatically sprayable substance for nasal or oral inhalation. Electrical charge is imparted to the spray particles by applying a high voltage to the substance prior to break up into a spray. In one embodiment, the device includes a nozzle portion for registry with the nasal or oral cavity and defines a passageway through which, in use, air can be drawn by inhalation on the part of the user. The substance to be sprayed passes into the passageway so that, with the assistance of user-induced air flow through the passageway, the resulting spray passes into the oral or nasal cavity.

28 Claims, 6 Drawing Sheets

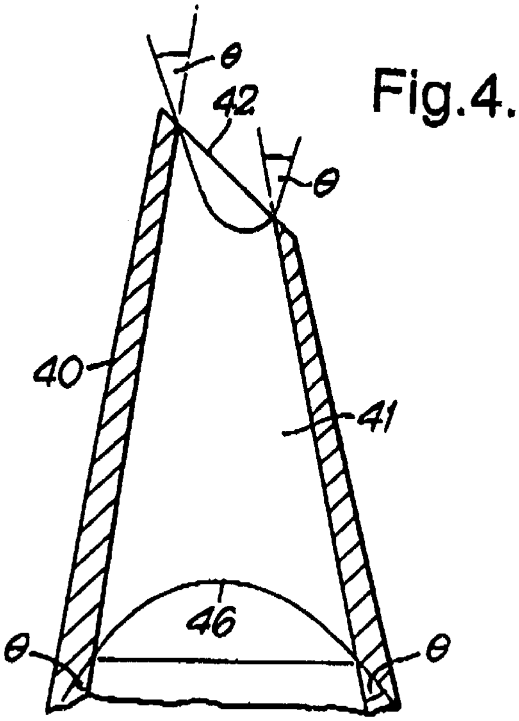
Fig.4.
Fig.5.
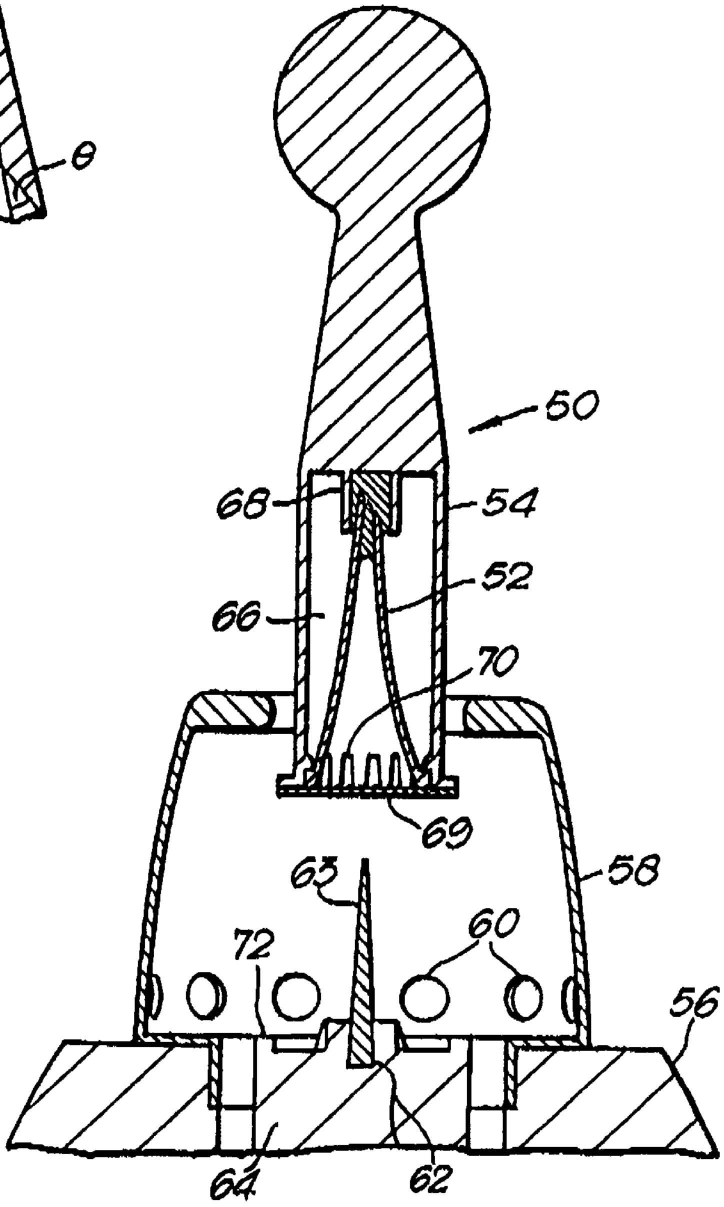

ELECTROSTATIC SPRAYING

This is a continuation under 35 U.S.C. Section 120 of International application PCT/GB96/01286 which designated the United States, filed internationally on May 30, 1996.

FIELD OF THE INVENTION

This invention relates to electrostatic spraying. The invention has particular application to, but is not limited to, the administration of pharmaceutical and therapeutic substances to the respiratory tract.

BACKGROUND OF THE INVENTION

As discussed in International Patent Application No. WO 94/19042, it is known that the site of deposition within the respiratory tract of an inhalable substance can be influenced by the level of electrostatic charge on the particles of the inhalable substance. International Patent Application No. WO 94/19042 discloses a device in which the substance to be administered is dispensed in the form of inhalable particles into a passageway defined by a mouthpiece of the device and an arrangement of electrodes within the passageway is used to impart electrostatic charge to the particles so dispensed. In this way, the electrostatic charge characteristically imparted to particles on being dispensed from a particular type of dispensing means can be modified in a controlled manner as they pass through a charging region established by the electrode arrangement. Such modification is stated to encompass increases, reductions, reversal and neutralisation of the level of electrostatic charge on the particles.

With such an arrangement, it is difficult to secure a uniform level of electrostatic charge on the particles since the particles are dispersed into the inhaled airstream and passed through the electric field developed by the electrodes. Particles at different locations in the airstream therefore tend to receive difficult levels of electrostatic charge resulting in particles with a wide spectrum of electrostatic charge.

An inhaler is also known from EP-A-234842 in which a liquid spray is produced in such a way that the droplets inhaled are electrically discharged prior to inhalation. In this form of inhaler, the liquid is sprayed from a spraying edge by developing an intense electric field between the spraying edge and a shield electrode so that the liquid is drawn into a ligament which then breaks up into electrostatically charged spray droplets. The charge on the droplets is then neutralised prior to inhalation by means of a sharp discharge electrode.

SUMMARY OF THE INVENTION

The present invention is concerned with the nasal or oral delivery of a spray such that the particles of the spray are substantially uniformly charged so as to limit their extent of penetration into the user's respiratory tract.

According to one aspect of the present invention an electrostatic spraying device for dispensing an electrostatically sprayable substance comprises: a housing provided with a nozzle portion which is suitable for registry with the nasal or oral cavity and defines a passageway through which, in use, air can be drawn by inhalation on the part of the user; and means for causing the substance to enter the passageway whereby, with the assistance of user-induced air flow through the passageway, the resulting spray passes into the nasal or oral cavity, characterised in that the issuing means includes means for applying high voltage to the substance prior to issue thereof whereby the spray is in the form of electrically charged particles which remain electrically charged on passage from the nozzle portion into the nasal or oral cavity of the user.

By applying high voltage to the substance to be sprayed prior to issue, a substantially uniform level of electrostatic charge is imparted to all of the particles forming the spray. This is particularly important in the case of for example drugs to be administered to the upper respiratory tract, eg the nasal cavity, because such drugs may be unsuitable or induce an adverse reaction if inhaled into the lungs. The presence of a well-defined charge on the particles ensures that they will not penetrate beyond the upper respiratory tract since they will rapidly deposit on for instance the nasal cavity lining upon inhalation into the nasal cavity.

Preferably the issuing means is so arranged that the driving force for production of the spray is primarily the electric field; in this manner, dispensing of the substance is not possible in the absence of the applied voltage. With the arrangements disclosed in WO-A-94/19042, the spray is produced separately from the electrical charging arrangement thus giving rise, in the event of malfunction of the electrical circuitry, to the possibility of continued dispensing without accompanying modification of the level of electrostatic charge. In such event, wastage may occur as a result of the spray particle deposition at inappropriate sites along the respiratory tract.

The issuing means may include a source of the substance to be sprayed and means for passively feeding (as opposed to a positive feed involving moving components) the substance to a dispensing location at which the substance is formed into the electrostatically charged spray. Such passive feed means may for instance comprise a wick material or a capillary tube.

Alternatively, the issuing means may comprise a holder for locating a discrete quantity of the substance in the vicinity of the dispensing location and the arrangement may, if desired, be of a "one-shot" nature such that issue of substantially all of the discrete quantity occurs when the high voltage applying means is enabled. The substance may be supplied to the holder in discrete quantities by a dose metering arrangement which may be operated to supply each discrete quantity to the holder before or after each spraying operation.

For instance, in one arrangement, the discrete quantity may be supplied to the holder immediately in advance of the high voltage being applied. In an alternative arrangement, disabling of the high voltage on completion of a dispensing operation may be accompanied by recharging of the holder with a fresh, discrete quantity of the substance in readiness for the next dispensing operation.

Instead of recharging the holder with substance to be dispensed by means of a feed arrangement, the holder may be removable for replacement or for refilling. For instance, a pack of holders may be provided each preloaded with the substance to be dispensed, eg in a single dose quantity, in which case the user would assemble a holder to the device, administer the dose or doses as appropriate and then discard the holder. On next usage, the procedure would be repeated using a fresh holder from the pack.

In contrast with WO-A-94/19042 and EP-A-234842, the device of the present invention does not require a specially constructed electrode arrangement located downstream of the dispensing location at which the liquid or powder substance is formed into a spray. However, the nozzle portion may act as a form of electrode in the sense that it may be effective to modify the electric field in the vicinity of the dispensing location and thereby quench high voltage induced spraying until the nozzle portion is contacted with a relatively low potential (eg earth) such as the nostril or lips of the user. Thus, if the nozzle portion is composed of a material which is sufficiently insulating, a spray suppressing potential may be established on the nozzle portion as a result of stray corona resulting from the initial application of the high voltage. Alternatively, the nozzle portion may be of a semi-insulating material and a high voltage of the same polarity as that applied to the substance may be applied to the nozzle portion to establish a spray suppressing potential thereon. In each case, the spray suppressing effect of the nozzle portion is negated when it is “grounded” as a result of being brought into contact with the user’s nostrils or lips, as the case may be.

Presently it is preferred that the nozzle portion is composed of a good electrically insulating material as the inability of such material to conduct charge away can be advantageous in operation since a build up of charge on the nozzle portion will then tend to repel deposition of charged spray particles on to the nozzle portion.

Where the substance is dispensed as a liquid formulation from a holder for locating a discrete quantity of the substance in close proximity to the dispensing outlet, in one form of the invention, the holder is conveniently constituted by a tube (conveniently a capillary tube) having an outlet forming the dispensing outlet and the discrete quantity is held within the tube in the vicinity of the outlet. In a preferred embodiment of this form of the invention, the tube has an internal configuration such the discrete quantity of liquid is located with its upstream meniscus in contact with a non-cylindrical tapering section of the tube.

We have found that such an internal tapering capillary tube section is effective to hold the discrete quantity of liquid in place and provides a driving force which, as the liquid is depleted by spraying from the outlet, serves to draw/feed the remaining liquid by surface tension and/or other effects towards the outlet more positively than a parallel-sided capillary bore. In addition, this internally tapering arrangement can have the additional advantages of being self-priming when dipped into the liquid formulation, less vulnerable to the development of air locks and less sensitive to disturbances tending to break the capillary retainment (anti-bounce).

It is to be understood that the references to “liquid formulation” above are not restricted to single phase media such as solutions, but also includes liquid-based media such as emulsions and suspensions of finely divided solids in a liquid.

In general, the dispensing outlet will be located upstream of the forward extremity of the nozzle portion in the direction of airstream flow induced by inhalation on the part of the user. As the spray is generated within the nozzle portion, at least a proportion of the electrically charged particles will have a tendency to deposit on to the nozzle portion as the latter will be at low potential when contacted with the user’s nostril or lips. Preferably therefore means is provided for securing a spray of relatively narrow swath directed generally paraxially of the passageway defined by the nozzle portion. Deposition of particles on the nozzle portion can be much reduced by such an expedient, especially if the arrangement is such that the extent of spray divergence is kept small over the distance between the dispensing location and an opening at the forward end of the nozzle portion.

In one embodiment intended to reduce deposition on the nozzle portion, the substance is dispensed from a tube one end of which forms a dispensing outlet from which the material issues, the tube end being of asymmetric configuration such that the tube has a leading extremity at one side thereof from which spraying is favoured. The asymmetric configuration may be achieved by imparting to the tube at the outlet end, an obliquely extending end face which intersects the outer peripheral surface of the tube at different axial locations thereby forming a leading extremity which is acute-angled. In this manner, the electric field can be intensified in the vicinity of the leading extremity thereby favouring spraying from this location. Typically, the angle at the leading extremity, ie the angle between the obliquely extending end face and the outer peripheral wall of the tube is within the range 30 to 60° (eg 40 to 50°). The tube in this embodiment will be composed of an electrically insulating material so that, despite its acute angle extremity, it is not prone to producing any significant corona discharge.

The arrangement may be such that, in operation, the liquid is drawn from the capillary bore across the end face towards the outer peripheral surface of the tube. Because of the intensified electric field prevailing in the vicinity of the leading extremity, the liquid is preferentially drawn into a number of ligaments from an edge portion in the locality of extremity and thereafter breaks up into droplets to form the spray. In general, the ligaments issue from the edge at angles bisecting the surfaces flanking the site of ligament formation. It will be understood that by favouring ligament formation at one side of the tube by producing it with an asymmetric configuration, the ligaments can be projected at angles closer to the axis of the tube.

According to a second aspect of the invention there is provided an electrostatic spraying device comprising a holder for retaining a discrete quantity of liquid to be sprayed, the holder having an outlet from which the liquid is dispensed in use, and means for applying high voltage to liquid within the holder so that the liquid droplets forming the spray are electrically charged, the holder having an internally tapering section which reduces in cross-section in a direction towards the outlet and the arrangement being such that the trailing meniscus of the discrete quantity of liquid contacts the tapering section.

According to a third aspect of the present invention there is provided a method of electrostatic spraying in which a discrete quantity of liquid to be sprayed is held within a holder which has an outlet from which the liquid discharges and an internally tapering configuration which reduces in cross-section towards the outlet, said quantity of liquid having its trailing meniscus in contact with the taper, and in which high voltage is applied to said discrete quantity so that the droplets of the resulting spray obtained from the outlet are electrically charged.

Where the context admits, any one or more of those features disclosed hereinbefore and also in the following description may be combined with the device and/or method as defined in said second and third aspects of the invention.

BRIEF DESCRIPTION OF THE DRAWINGS

The invention will now be described by way of example with reference to the accompanying drawings, in which:

FIG. 4 is an enlarged view showing the capillary section of the spraying tip;

FIG. 5 is a diagrammatic view showing another form of device in accordance with the invention;

DETAILED DESCRIPTION OF THE INVENTION

Figure 1:
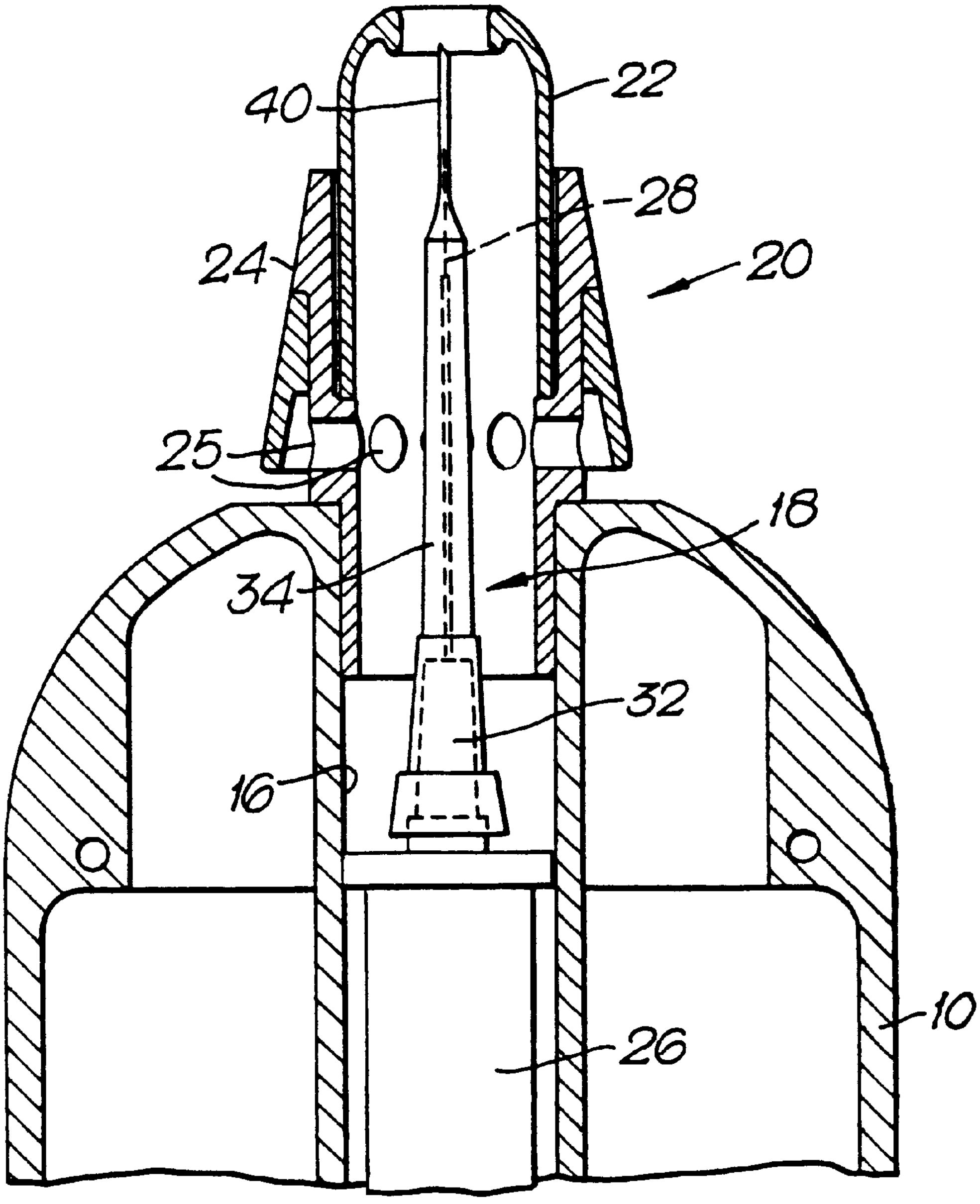
FIG. 1 is a diagrammatic view showing part of a nasal sprayer according to the present invention.
Figure 2:
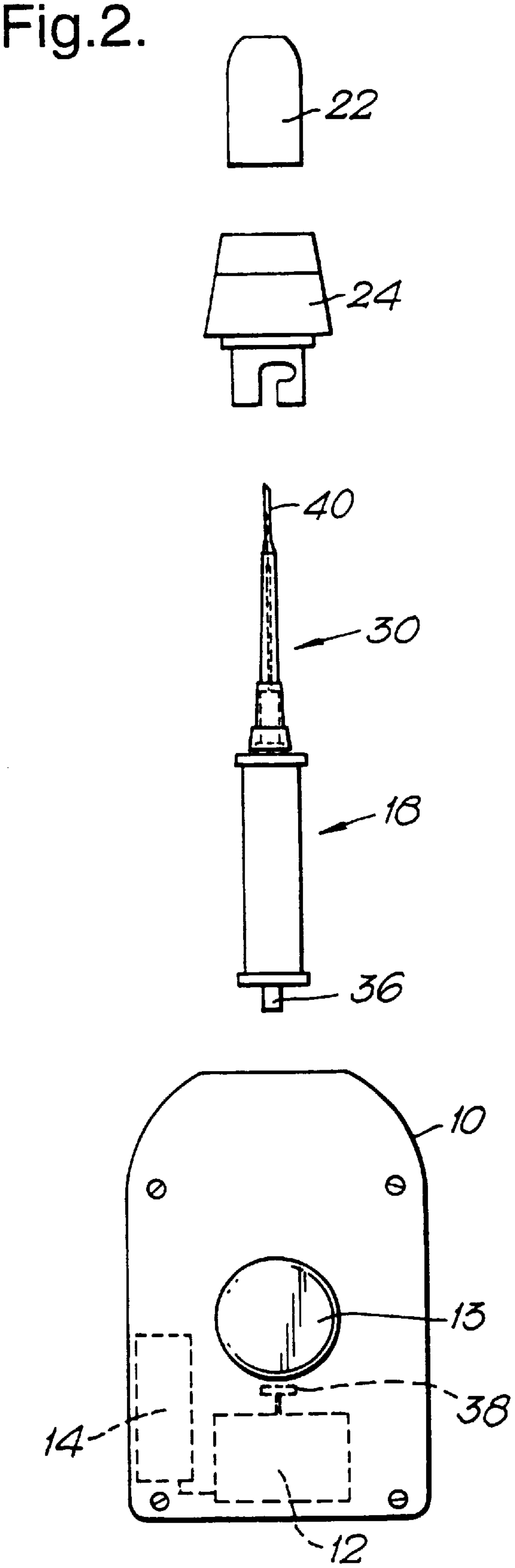
FIG. 2 is an exploded view showing components of the device illustrated in FIG. 1.
Figure 3:
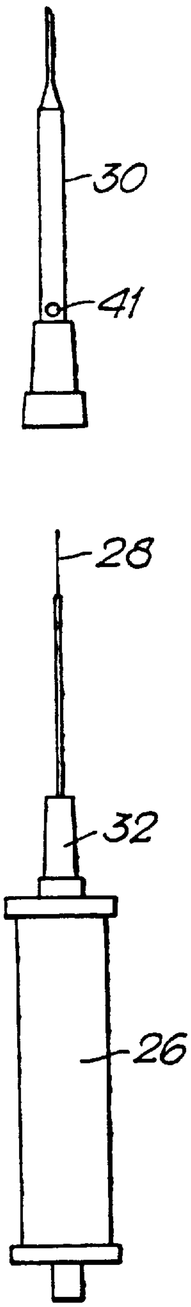
FIG. 3 is an exploded view showing components forming the spraying tip assembly of the device show in FIGS. 1 and 2.

Referring to FIGS. 1 to 4, the nasal sprayer comprises a housing 10 suitably dimension for handheld use. The housing accommodates a high voltage generator 12 and a low voltage battery supply 14 for powering the generator. The battery supply may comprise one or more replaceable batteries which may be of the rechargeable type if desired. The generator typically produces a high voltage output from about 2 to 3 kV up to about 12 to 15 kV, preferably from 3 or 4 kV to about 9 to 10 kV. Operation of the generator 12 is controlled by means of a switch suitably positioned for operation by the user while holding the device in one hand. In this embodiment, the switch is in the form of a pushbutton type switch 13 located centrally of the housing for ease of operation with the thumb or other fingers while holding the device in the palm of the hand. An earth return path may be established through the user for example by providing some form of contact on the housing so that the act of holding the device in the hand provides the connection to earth through the user, for instance in the manner disclosed in EP-A-120633.

The housing is fabricated from a good insulating plastics material and is designed in accordance with the teaching of our prior EP-A-441501 in order to allow the use of an inexpensive and compact generator. A central bore 16 is formed within the housing and a spray tip assembly 18 is removably inserted into the bore 16. The forward end of the bore 16 receives a nozzle assembly 20 comprising a nose piece 22 which fits, eg as a snap fit, within an outer body 24 formed with one or more apertures 25 through which air can be drawn by the user in the course of inhaling through the nose. The outer body 24 fits into the bore 16 and is arranged to be releasably connected to the housing in any suitable manner, eg by means of a bayonet connection. Removal of the nozzle assembly 20 permits removal of the spray tip assembly 18. Both the nose piece 22 and the outer body 24 are preferably formed from a good electrically insulating material such as a suitable plastics material.

The spray tip assembly 18 comprises a holder 26 from which a thin HT wire 28 projects and a tip section 30 which can be engaged, for instance as an interference fit, with a spigot section 32 of the holder 26. The HT wire 28 is supported by a metal support sleeve 34 over the major part of its projecting length and passes through the holder 26 for connection to a contact 36 which, in turn, engages a contact 38 to which the high voltage output of the generator is connected.

The tip section 30 may be in the form of a so-called loader tip as used for pipettes (manufactured by Eppendorf GmbH of Germany). It is of tubular configuration for reception of the HT wire 28 and terminates in a capillary tube section 40 into which the leading end of the HT wire extends. The capillary section 40 serves to receive and hold a small quantity of liquid to be sprayed (usually up to about 20 μl, typically 1 to 10 μl) and an unsupported length of the thin HT wire 28 is arranged to extend into the capillary section 40 in order to connect the high voltage output of the generator to the bulk liquid within the capillary section. Typically the liquid to be sprayed will have a resistivity (at 25° C.) in the range $1\times10^4$ to $1\times10^9$ ohm cm. A typical liquid formulation comprises oxymetazoline in for example an aqueous or alcohol based diluent, with suitable resistivity and viscosity properties for electrostatic spraying. If necessary, viscosity and/or resistivity adjusting additives may also be incorporated in the formulation. Upstream of the capillary section 40, the tip section is formed with an air vent 41 so that, during depletion of the liquid as spraying proceeds, air can enter the tip section upstream of the trailing meniscus of the volume of liquid contained in the capillary section 40.

As illustrated, the HT wire terminates short of the leading end of the capillary section 40 in order to avoid unduly restricting the diameter of the capillary section in the immediate vicinity of its outlet and also to avoid creating any undesirable surface tension effects which could otherwise impede delivery of the liquid from the capillary section. Even though the HT wire 28 terminates at a location upstream of the outlet of the capillary section, spraying can nevertheless still continue, albeit at a reduced rate, even after the trailing meniscus of the liquid volume has moved past the leading end of the HT wire. This is because electrical charge can still be transmitted from the HT wire to the liquid by corona discharge effects and may also leak along the inner surfaces of the capillary section. Although, in the illustrated embodiment, the high voltage is conducted to the liquid via the HT wire, it will be understood that other possibilities exist. For instance, the spray tip section could be fabricated with a conductive track along its length for conduction of the high voltage to the liquid.

The forward end of the capillary tube section 40 has an obliquely extending end face 42 produced by cutting the capillary tube section obliquely whereby the end face 42 extends in a plane which intersects the outer peripheral surface of the tube at different axial locations thereby forming a leading extremity which is acute-angled. In this manner, the electric field is intensified in the vicinity of the leading extremity thereby favouring spraying from this location. Typically, the angle q at the leading extremity is within the range 30 to 60° (eg 40 to 50°).

In operation, the liquid is drawn from the capillary section 40 across the end face 42 towards the outer peripheral surface of the tube. Because of the intensified electric field prevailing in the vicinity of the leading extremity, the liquid is preferentially drawn into one or more ligaments from an edge portion in the locality of extremity and thereafter breaks up within the nosepiece into droplets to form the spray. In general, the ligament or ligaments issue from the edge at angles bisecting the surfaces flanking the site of ligament formation. It will be understood that by favouring ligament formation at one side of the tube by producing it with an asymmetric configuration, the ligament or ligaments can be projected paraxially, ie at angles closer to the axis of the tube compared with a tube configuration in which the end of the tube is perpendicular to the tube axis. By producing a ligament which is projected generally paraxially, there is a reduced tendency for spray particles within the nosepiece to be attracted towards, and deposit onto, the nose piece when the latter is grounded by contact with the user's nostril.

The tendency for deposition on the nozzle assembly during spraying can also be reduced by fabricating the nose piece from a good electrically insulating material which will tend to hold any charge that it collects during spraying. Thus, when spraying commences corona effects lead to some charge deposition on the nose piece which, in turn, tends to repel the like-charged spray particles.

Preferably the portion of the spray tip in which the liquid is received, ie the capillary section 40, is designed to provide a positive driving force which urges the liquid towards the forward end of the capillary section as spraying proceeds. As shown in FIG. 4, this is achieved by producing the capillary section with an internal taper such that the cross-sectional area of the capillary section increases in a direction away from its forward end. The internal taper may be obtained for example by drawing out the capillary tube section. The taper is such that the trailing meniscus 46 of the liquid is in contact with a tapering portion of the capillary section.

For reasons that are not fully understood, but may be related to effects such as surface tension effects and pressure differentials acting on the leading and trailing menisci of the liquid, we have found that such an arrangement is effective to drive the liquid forwardly to the end of the capillary section during liquid spraying. Thus, as the volume 41 of liquid becomes depleted by spraying, the remaining volume is driven forwardly more positively than would be the case with a capillary section having a cylindrical bore. Also, compared with a cylindrical capillary bore, a tapering capillary bore has been found to be less sensitive to disturbance which could otherwise lead to an air bubble becoming trapped in the capillary section and the positive drive effect tends to eliminate any bubbles that may occur. It will be understood that whilst the upper and lower menisci of the liquid will have the same angle of contact 0 with the internal surface of the tube, when the surface tension force is resolved in the axial direction, the force acting in the vicinity of the upper meniscus will be greater than that acting in the vicinity of the lower meniscus. This difference may be a factor in effecting drive of the liquid forwardly.

When the liquid has been dispensed, the tip section 30 may either be removed for replacement with a similar tip section containing a fresh charge of liquid or alternatively it may be recharged with liquid and reassembled. Recharging can be effected for instance by dipping the end of the spray section into the liquid so that it takes up a small quantity. It will be understood that the device is not limited to use with only one liquid formulation. It may be used for instance with a range of spraying tips each containing different liquid formulations and/or different amounts of the liquid formulation, depending on the type of treatment required.

In use, it will be understood that the user will insert the nose piece 22 into the nostril and, while inhaling, will operate the switch 13 to energise the generator and cause spraying of the liquid. By virtue of the technique used for producing the spray, the spray particles will be uniformly charged and the act of inhaling/sniffing will produce an airflow which assists drawing the spray into the nasal cavity. Because the particles are electrically charged, they will rapidly deposit on the lining of the nasal cavity or within the upper respiratory tract thereby ensuring that penetration of the particles is limited.

Referring now to FIG. 5, this illustrates an alternative arrangement for assembling pre-loaded spraying tips to a device similar to that of FIGS. 1 to 4. In this instance, the spraying tip 50 is fabricated as a unit comprising a capillary section 52 (preferably internally tapered and formed with an oblique end face as described with reference to FIGS. 1 to 4) and a carrier 54 by means of which the spraying tip can be manipulated during assembly to the device. The device in this case is shown schematically and comprises a housing 56 provided with a nose or mouth piece 58 with air inlet apertures 60. The housing 56 accommodates a power source (eg a battery pack) and a high voltage generator, the output of which is connected by lead 62 to a sharp electrode 63 mounted on a holder 64 assembled to the housing.

The carrier 54 has a cavity 66 in which the capillary section 52 tip is received with the larger diameter end of the latter closing the cavity. The carrier and capillary section are connected together, eg by adhesive or otherwise, in such a way that the two components are axially captive with one another but can be separated by rotating one relative to the other to sever the connection however made. The smaller diameter end of the capillary section 52 contains a unit dose of a drug or the like to be dispensed and is received within a recess 68 forming a sealing arrangement with the end of the capillary section 52. The larger diameter end of the capillary section is covered by a layer of metal foil 69 and one or more vent holes 70 are provided in the side wall of the capillary section at this location. The holes 70 serve to admit air into the capillary section 52 during spraying and are also arranged to register with complementary formations 72 provided on the forward end of the holder 64.

Assembly of the spraying tip 50 to the device entails inserting the unit through the opening in the nose or mouthpiece 58 so as to register the holes 70 and the formations 72 thereby making the capillary section rotationally captive to the holder 64. At the same time, the electrode 63 pierces the metal foil layer 69 and enters the capillary section to allow charging of the liquid contained at its forward end. Once the capillary section has been properly registered with the holder 64, the carrier 54 is twisted to release it from the capillary section thus allowing the carrier to be withdrawn, leaving the capillary section in place. Spraying operation of the liquid can then be effected in the manner described in connection with FIGS. 1 to 4. When the capillary section 52 is spent, it can be removed by first removing the nose or mouth piece. A fresh unit is then used to attach a new capillary section to the device.

Although the embodiment of FIG. 5 is described with reference to dispensing of a liquid formulation, it will be understood that the substance to be dispensed may instead be in powder form. In this event, the arrangement may be such that the mass of powder is retained at the forward end of the section 52 by a suitably located layer of metal foil which is pierced by the electrode 63 during assembly of the spraying tip to the device. In this case, the layer 69 may be dispensed with.

Figure 6:
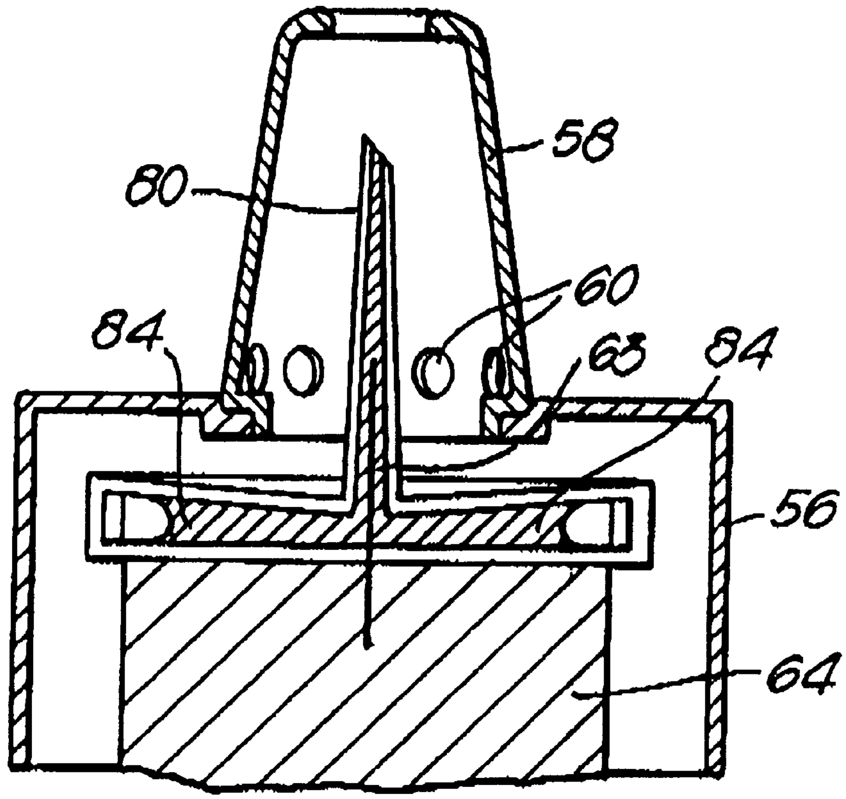
FIG. 6 is a diagrammatic view of further form of the invention intended for multi-dose applications.
Figure 7:
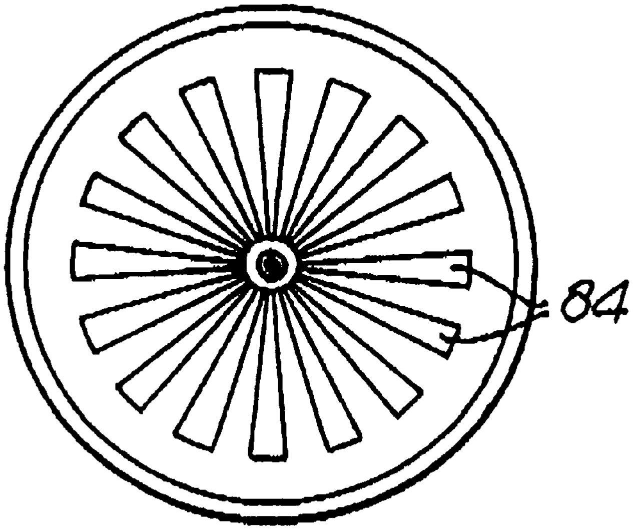
FIG. 7 is a plan view illustrating the arrangement of the liquid supply passageways in the spraying tip of the embodiment in FIG. 6.

FIGS. 6 and 7 show a multi-dose arrangement. The components of the device may be generally the same as in the embodiment of FIG. 5 and the same reference numerals are used to identify like components. In this instance, the spraying tip comprises a forwardly projecting capillary section 80 into which the electrode 63 projects when the spraying unit is properly assembled to the holder 64, and a base unit 82. The base unit 82 is formed with a series of radial capillary passageways 84 of tapering configuration such that the cross-sectional area of each passageway increases radially outwardly. At their radially inner ends, the passageways communicate with the capillary section 80 and at their radially outer ends the passageways are formed with a vent hole (not shown) for the admission of air. The spraying tip is filled with liquid to be sprayed and it will be seen that initially the liquid fills the forwardly projecting section 80 and a substantial proportion of each passageway 84. Because the section 80 and the passageways are of internally tapering configuration, the liquid is subjected to a positive drive force tending to feed the liquid to the outlet of the section 80 as liquid is sprayed from the outlet in use.

Figure 8:
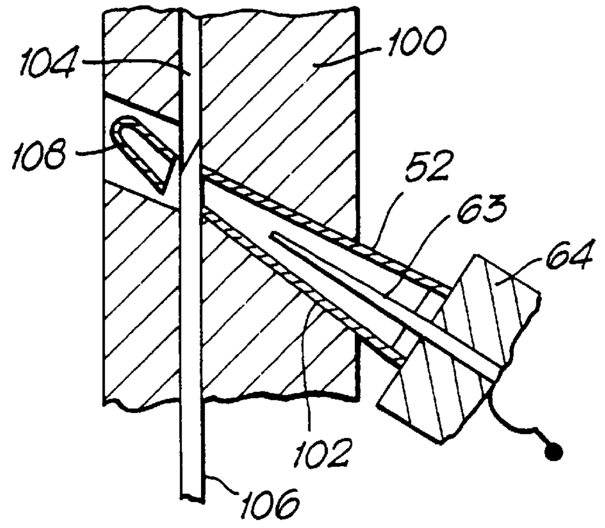
FIG. 8 is a diagrammatic view illustrating production of an oblique end face on a spraying tip.
Figure 9:
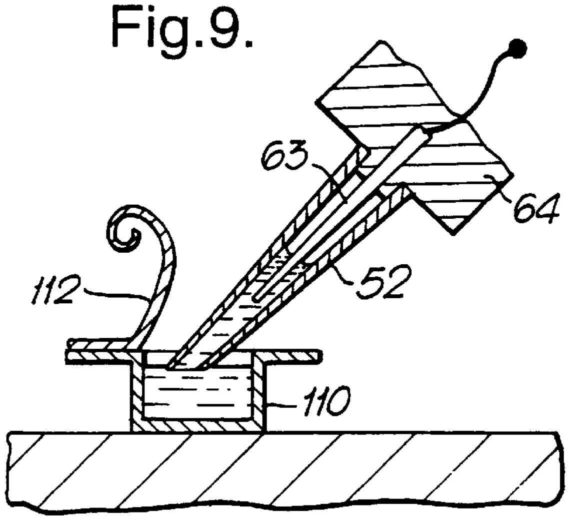
FIG. 9 is a diagrammatic view illustrating priming of a spraying tip.

Referring to FIGS. 8 and 9, the spraying tip may initially be supplied as a sealed unit (with or without liquid to be sprayed) for assembly to the holder 64 in the manner described with reference for example to FIG. 5, ie with the forward extremity of the capillary section closed. In this event, a special tool may be supplied with the device for unsealing the spraying tip and at the same time producing an oblique end face at the outlet of the capillary section 52. As shown in FIG. 8, the tool comprises a body 100 with an opening 102 for reception of the capillary section 52. The opening 102 intersects a slot 104 along which a shearing blade 106 is movable by the user. As the blade 106 moves along the slot, it severs the forward extremity 108 of the capillary section 52 to expose the interior thereof.

FIG. 9 illustrates charging of liquid into the capillary section by immersing the tip of the capillary section 53 into liquid contained in a foil sealed capsule 110 after peeling back the foil layer 112. After the capillary section 53 has been charged with liquid, the holder 64 and attached spraying tip are then assembled to the device together with the nose or mouth piece so that spraying can be effected in the manner generally described with reference to FIGS. 1 to 4.

Figure 10:
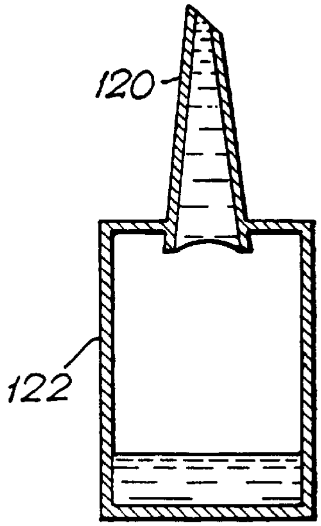
FIG. 10 is a diagrammatic view of a multi-dose spraying tip.

FIG. 10 illustrates a multi-dose spraying tip comprising internally tapering capillary section 120 terminating in an oblique end face. In this embodiment, the spraying tip includes a receptacle 122 for liquid to be sprayed. By appropriate manipulation of the spraying tip, ie shaking and/or inversion etc, part of the liquid can be caused to lodge in the capillary section 120 for spraying. It will be understood that the embodiment of FIG. 10 will be appropriately designed to allow it to be assembled to a holder such as that described with reference to FIG. 5 whereby an electrode penetrates into the capillary section 120 to conduct the high voltage thereto necessary to effect spraying.

Figure 11:
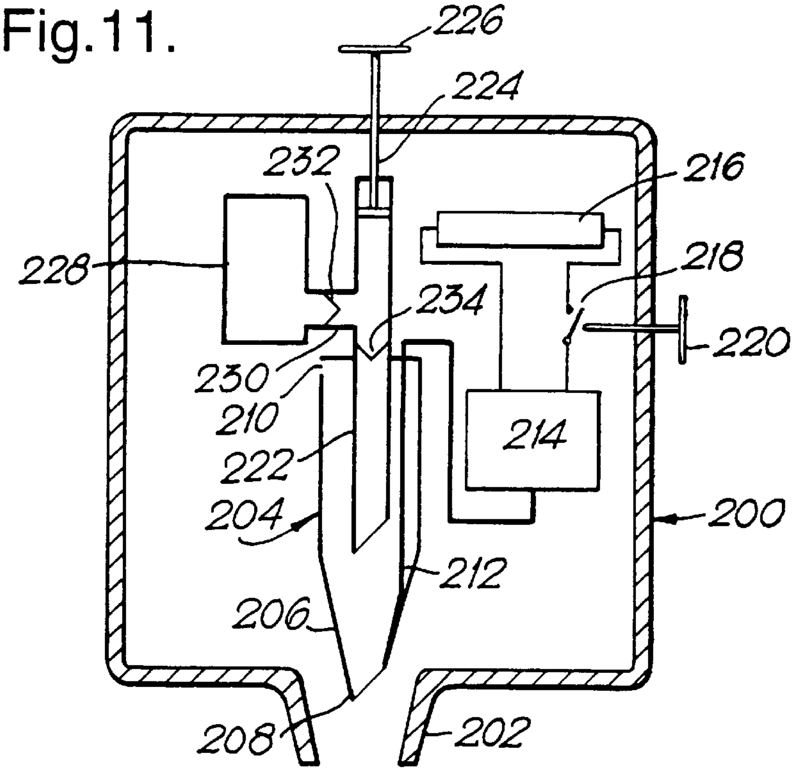
FIG. 11 is a diagrammatic view of another embodiment of spraying device in accordance with the invention.

Referring now to FIG. 11, this illustrates schematically a nasal sprayer for use in electrostatically spraying nasal formulations, the sprayer comprising a housing 200, suitably dimensioned for handheld use, formed with a nose piece 202. Although not shown, the housing may include one or more suitably located openings to provide air ingress so that an air flow can be induced by inhaling through the nose piece in use. A tube 204 formed with a tapering capillary section 206 is mounted within the housing 200 with its tip 208 located in the vicinity of the nose piece, the tip being formed with an oblique configuration for the reasons specified in connection with the embodiment of FIGS. 1 to 4. An air vent 210 is provided in the tube 208. Electrode 212 extends along the tube 204 and terminates adjacent the tip 208. The electrode 212 is connected to the high voltage output (e.g. 3 to 15 kV) of voltage generator 214 which is powered by a DC battery supply 216 (e.g. 9 V) under the control of switch 218 and a user-operable actuator 220 accessible externally of the housing. The switch 218 is biased to the open position by suitable means such as a spring. A suitable earth return path for the device may be provided via the user of the device, in any convenient manner—e.g. as disclosed in connection with the embodiment of FIGS. 1 to 4.

Dosing of the capillary section 206 is effected by means of a user-operable syringe device comprising tube 222 fitted with a plunger 224 terminating in a user-operable button 226 external to the housing. The plunger is biased to a retracted position by suitable means such as a spring (not shown). A receptacle 228 containing the formulation to be sprayed is connected to the tube 222 via inlet 230 controlled by one-way valve 232 so arranged that return movement of the plunger 224 from an extended position to the retracted position shown is effective to draw liquid from the receptacle 228 through inlet 230 into the tube 222. Subsequent operation of the plunger by the user by depression of the button 226 then displaces the liquid in tube 222 past a one-way valve 234 for injection into the tapering capillary section 206 thereby charging the latter with a dose of the formulation to be sprayed. It will be appreciated that the volume of the dose injected in this manner will be such that the trailing meniscus of the liquid slug introduced into section 206 contacts the tapering side wall of the latter. On release of the button 226, the plunger will retract again and draw further liquid from the receptacle 228 into the tube 222 upstream of valve 234. Although the valve 234 is shown at being situated close to the inlet 230, it will be appreciated that this is not essential and that valve 234 could be located at any suitable point downstream of the inlet 230, e.g. close to the open end of the tube 222 if desired.

Once the capillary section 206 has been charged in this manner, the dose can then be dispensed by electrostatic spraying in the manner described above in relation to the embodiment of FIGS. 1 to 4. In practice, the user will orientate the sprayer so that the nose piece 202 is lowermost during charging of the capillary section 206. Once charging has been accomplished, the user will then invert the device, register the nose piece appropriately and depress actuator 220 to operate the voltage generator and hence initiate electrostatic spraying. During inversion of the device, the charge held by the capillary section 206 will remain in place by virtue of surface tension.

The receptacle 228 will usually be in the form of a replaceable cartridge adapted to be fitted to the inlet 230 and the housing may include a removable or hingeable cover to allow access to the cartridge for replacement purposes. Likewise access will be provided for replacement of the battery 216.

Figure 12:
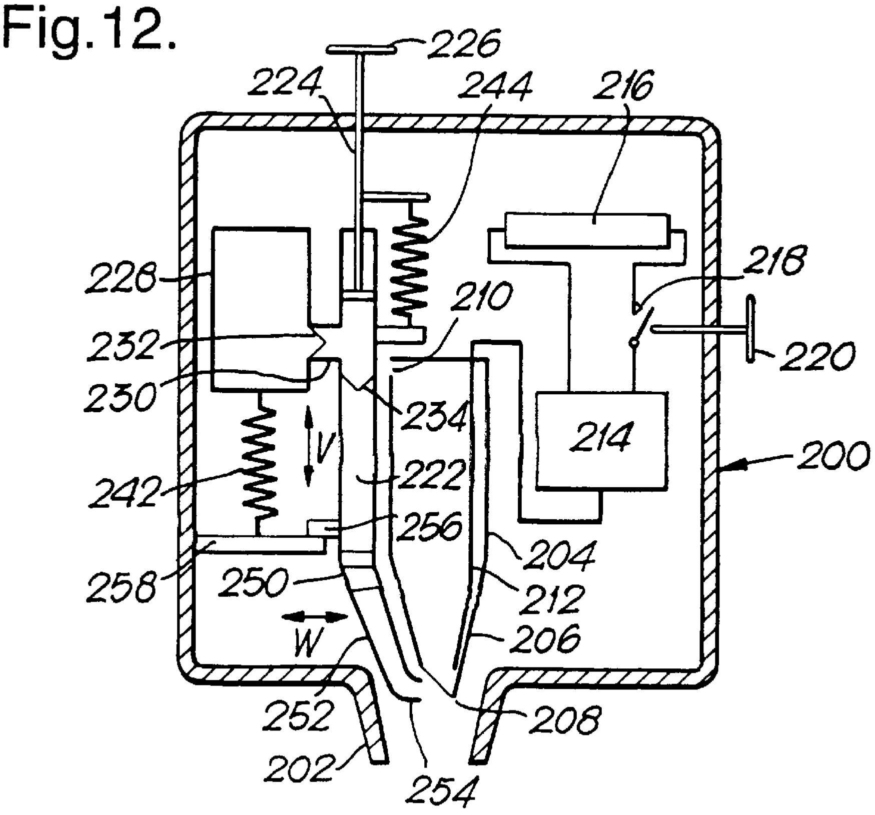
FIG. 12 illustrates a modification of the spraying device shown in FIG. 11.

The embodiment of FIG. 11 is orientation sensitive during charging of the capillary section. FIG. 12 illustrates a modification which is not orientation sensitive and also provides charging of the tapering capillary section from its smaller diameter end. Those parts in FIG. 12 which are similar to those in the embodiment of FIG. 11 are depicted by the same reference numerals. In this instance, the tube 222 of the syringe device is located externally of the tube 204 and terminates in a discharge opening 254. The assembly comprising the tube 222 and receptacle 228 is mounted for movement relative to the housing 200 in a generally vertical direction (as indicated by arrows V) as viewed in FIG. 12 between a first position as shown in which the discharge opening 254 is located immediately adjacent the tip 208 for delivery of a charge of liquid into the tapering capillary section 206 and a retracted position. The assembly is biased to the retracted position by suitable means such as a compression spring 242, the arrangement being such that the biasing means acting on the assembly of tube 222 and receptacle 228 is weaker than the biasing means, e.g. compression spring 244, acting between the plunger 224 and the tube 222.

The tube 222 in this embodiment has a flexible joint 250 which allows some movement of the tube section 252 in the direction indicated by arrows W but biases the tube section 252 to the right as viewed in FIG. 12 so that as the tube 222 moves downwardly as viewed in FIG. 12, the outlet 254 of tube 222 moves into close proximity with the open tip 208 of the tube section 206.

The sequence of operation is as follows. Assuming that the tube 222 has been primed with liquid upstream of valve 234, to prime the capillary section 206 button 226 is depressed. Initially, because of the difference in spring rates of springs 242 and 244, spring 242 deforms and allows depression of button 226 to be translated into downward movement of the receptacle 228 and tube 222 until a projection 256 on tube 222 abuts stop 258. At this point, outlet 254 will be located immediately adjacent tip 208. Continued depression of button 226 is now effective to deform spring 244 causing plunger 224 to move relative to the tube 222 with consequent transfer of liquid past the valve 234 and into the capillary section 206 via outlet 254. Release of the button at this stage results in return movement of the receptacle 228 and tube 222 to the retracted position in which the outlet 254 is clear of the tip 208. In the course of the return movement, the plunger 224 is also caused to retract by spring 244 with consequent further priming of the tube 222 via the one way valve 232. Once button 226 has been released, the user can dispense the formulation in the form of spray of electrically charged droplets by operating the button 220.

In the embodiments thus far described, the high voltage generator is assumed to be unipolar; however, if desired, it may have a bipolar output as disclosed in EP-A-468735 and EP-A-468736.

What is claimed is:

1. An electrostatic spraying device for dispensing an electrostatically sprayable substance comprising:

a housing provided with a nozzle portion which is suitable for registry with the nasal or oral cavity and defines a passageway through which, in use, air can be drawn by inhalation on the part of the user; and issuing means for causing the substance to enter the passageway whereby, with the assistance of user-induced air flow through the passageway, the resulting spray passes into the nasal or oral cavity, characterised in that the issuing means includes a holder for locating a discrete quantity of the substance in the vicinity of the dispensing location and includes means for applying high voltage to said discrete quantity of the substance prior to issue thereof from said holder whereby the spray is in the form of electrically charged particles which remain electrically charged on passage from the nozzle portion into the nasal or oral cavity of the user.

2. A device as claimed in claim 1 in which the issuing means includes a source of the substance to be sprayed and means for feeding a discrete amount of the substance to said holder.

3. A device as claimed in claim 1 in which the holder is constituted by a tube having an outlet forming the dispensing outlet and the discrete quantity is held within the tube in the vicinity of the outlet.

4. A device as claimed in claim 3 in which the holder is constituted by a capillary tube.

5. A device as claimed in claim 3 in which the tube has an internal configuration such the discrete quantity of liquid is located with its upstream meniscus in contact with a non-cylindrical tapering section of the tube.

6. A device as claimed in claim 1 in which the dispensing outlet is located upstream of the forward extremity of the nozzle portion in the direction of airstream flow induced by inhalation on the part of the user.

7. A device as claimed in claim 1 including means for securing a spray of relatively narrow swath directed generally paraxially of the passageway defined by the nozzle portion.

8. A device as claimed in claim 1 in which the substance is dispensed from a tube one end of which forms the outlet from which the substance issues, the tube end being of asymmetric configuration such that the tube has a leading extremity at one side thereof from which spraying is favoured.

9. A device as claimed in claim 1 in which the device is in the form of a self-contained unit comprising a housing which is suitable for hand-held use or is readily portable using one hand.

10. A device as claimed in claim 1 in which the arrangement is such that the applied voltage is insufficient to cause spraying until the electric field is sufficiently intensified by bringing the substance to be sprayed into the proximity of an object or target towards which the substance is to be sprayed.

11. A device as claimed in claim 1 in which the substance comprises a liquid formulation.

12. A device as claimed in claim 1 in which the substance comprises a solid in liquid suspension.

13. A device as claimed in claim 1 in which the applied voltage is positive.

14. A device as claimed in claim 1 in which the high voltage is bipolar.

15. A device as claimed in claim 1 in which the volume of said discrete quantity is up to 50 $\mu$l.

16. A device as claimed in claim 1 in which the volume of said discrete quantity is up to 20 $\mu$l.

17. A device as claimed in claim 1 in which the high voltage is in the range 2 to 15 kV.

18. A device as claimed in claim 1 in which the high voltage is in the range of 3 to 15 kV.

19. A device as claimed in claim 1 in which the high voltage is in the range of 4 to 10 kV.

20. An electrostatic spraying device comprising a holder for retaining a discrete quantity of liquid to be sprayed, the holder having an outlet from which the liquid is dispensed in use, and means for applying high voltage to said discrete quantity of liquid within the holder so that the liquid droplets forming the spray are electrically charged, the holder having an internally tapering section which reduces in cross-section in a direction towards the outlet and the arrangement being such that the trailing meniscus of the discrete quantity of liquid contacts the tapering section.

21. A device as claimed in claim 20 in which the holder comprises a capillary tube.

22. A device as claimed in claim 20 in which the device includes a housing provided with a nozzle and in which the holder is located with the outlet thereof in registry with the nozzle and upstream of the forward extremity of the nozzle in the direction of spraying.

23. An electrostatic spraying device comprising a holder for retaining a charge of liquid to be sprayed, the holder having an outlet from which the liquid is dispensed in use, means for applying high voltage to said charge of liquid within the holder so that the liquid droplets forming the spray are electrically charged, the holder having an internally tapering section which reduces in cross-section in a direction towards the outlet, and means for introducing a charge of liquid into the holder such that the trailing meniscus of the discrete quantity of liquid contacts the tapering section.

24. An electrostatic spraying device for dispensing an electrostatically sprayable substance comprising:

a housing provided with a nozzle portion which is suitable for registry with the nasal or oral cavity and defines a passageway through which, in use, air can be drawn by inhalation on the part of the user; and issuing means for causing the substance to enter the passageway whereby, with the assistance of user-induced air flow through the passageway, the resulting spray passes into the nasal or oral cavity, characterised in that the issuing means includes means for applying high voltage to the substance prior to issue thereof whereby the spray is in the form of electrically charged particles which remain electrically charged on passage from the nozzle portion into the nasal or oral cavity of the user and means is provided for securing a spray of relatively narrow swath directed generally paraxially of the passageway defined by the nozzle portion.

25. An electrostatic spraying device for dispensing an electrostatically sprayable substance comprising:

a housing provided with a nozzle portion which is suitable for registry with the nasal or oral cavity and defines a passageway through which, in use, air can be drawn by inhalation on the part of the user; and issuing means for causing the substance to enter the passageway whereby, with the assistance of user-induced air flow through the passageway, the resulting spray passes into the nasal or oral cavity, characterised in that the issuing means includes means for applying high voltage to the substance prior to issue thereof whereby the spray is in the form of electrically charged particles which remain electrically charged on passage from the nozzle portion into the nasal or oral cavity of the user and the substance is dispensed from a tube one end of which forms the outlet from which the substance issues, the tube end being of asymmetric configuration such that the tube has a leading extremity at one side thereof from which spraying is favoured.

26. An electrostatic spraying device for dispensing an electrostatically sprayable substance comprising:

a housing provided with a nozzle portion which is suitable for registry with the nasal or oral cavity and defines a passageway through which, in use, air can be drawn by inhalation on the part of the user; and issuing means for causing the substance to enter the passageway whereby, with the assistance of user-induced air flow through the passageway, the resulting spray passes into the nasal or oral cavity, characterised in that the issuing means includes means for applying high voltage to the substance prior to issue thereof whereby the spray is in the form of electrically charged particles which remain electrically charged on passage from the nozzle portion into the nasal or oral cavity of the user, the arrangement being such that the applied voltage is insufficient to cause spraying until the electric field is sufficiently intensified by bringing the substance to be sprayed into the proximity of an object or target towards which the substance is to be sprayed.

27. A method of electrostatic spraying in which a discrete quantity of liquid to be sprayed is held within a holder which has an outlet from which the discrete quantity of liquid discharges and an internally tapering configuration which reduces in cross-section towards the outlet, said discrete quantity of liquid having its trailing meniscus in contact with the taper, and in which high voltage is applied to said discrete quantity of liquid so that the droplets of the resulting spray obtained from the outlet are electrically charged.

28. A method of electrostatic spraying comprising providing a holder having an outlet and an internally tapering configuration which reduces in cross-section towards the outlet, introducing a discrete volume of liquid into the holder so that the trailing meniscus of the discrete volume of liquid is in contact with the taper, and applying high voltage to the discrete volume of liquid so that the droplets of the resulting spray obtained from the outlet are electrically charged.

* * * * *